US010213153B2

(12) United States Patent
Atallah et al.

(10) Patent No.: US 10,213,153 B2
(45) Date of Patent: Feb. 26, 2019

(54) WEARABLE PAIN MONITOR USING ACCELEROMETRY

(71) Applicant: KONINKLIJKE PHILIPS N.V., Eindhoven (NL)

(72) Inventors: Louis Nicolas Atallah, Eindhoven (NL); Kiran Hamilton J. Dellimore, Eindhoven (NL); Marcel Cornelis Dirkes, Eindhoven (NL); Jens Mühlsteff, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 401 days.

(21) Appl. No.: 14/951,551

(22) Filed: Nov. 25, 2015

(65) Prior Publication Data

US 2016/0151013 A1 Jun. 2, 2016

(30) Foreign Application Priority Data

Nov. 27, 2014 (EP) .................................... 14195165

(51) Int. Cl.
*A61B 5/04* (2006.01)
*A61B 5/02* (2006.01)
(Continued)

(52) U.S. Cl.
CPC ........ *A61B 5/4824* (2013.01); *A61B 5/02438* (2013.01); *A61B 5/113* (2013.01); *A61B 5/6823* (2013.01); *A61B 5/7239* (2013.01); *A61B 5/0002* (2013.01); *A61B 5/0205* (2013.01); *A61B 5/02405* (2013.01); *A61B 5/0816* (2013.01); *A61B 5/1112* (2013.01);
(Continued)

(58) Field of Classification Search
USPC .................................................. 600/300–301
See application file for complete search history.

(56) References Cited

U.S. PATENT DOCUMENTS 6,659,968 B1 12/2003 McClure
8,512,240 B1 8/2013 Zuckerman-Stark
(Continued)

FOREIGN PATENT DOCUMENTS

WO 2007052108 A2 5/2007
WO 2010134068 A1 11/2010

OTHER PUBLICATIONS

Muehlsteff, J. et al, "Feasibility of Pulse Presence and Pulse Strength Assessment during Head-up Tilt Table Testing Using an Accelerometer located at the Carotid Artery" in Proceedings of EMBC 2014.
(Continued)

*Primary Examiner* — Nicole F Johnson

(57) ABSTRACT

A device and method for monitoring pain of a user (50) are presented. The device (10) comprises a receiving unit (12) for receiving an accelerometer signal (38) from an accelerometer sensor (30) worn by the user (50), wherein the accelerometer signal (38) comprises components of a pulse signal (20) and a respiration signal (22); and a processing unit (14) configured to: derive the pulse signal (20) and the respiration signal (22) from the accelerometer signal (38); adapt the pulse signal (20) based on the respiration signal (22) in order to obtain a corrected pulse signal (40); and derive a pain descriptor based on the corrected pulse signal (40).

15 Claims, 5 Drawing Sheets

(51) Int. Cl.
*A61B 5/00* (2006.01)
*A61B 5/113* (2006.01)
*A61B 5/0205* (2006.01)
*A61B 5/024* (2006.01)
*A61B 5/08* (2006.01)
*A61B 5/11* (2006.01)

(52) U.S. Cl.
CPC ........... *A61B 5/1118* (2013.01); *A61B 5/7278* (2013.01); *A61B 2562/0219* (2013.01)

(56) References Cited

U.S. PATENT DOCUMENTS

| | | | |
|---|---|---|---|
| 8,591,411 B2 | 11/2013 | Banet | |
| 2004/0015091 A1 | 1/2004 | Greenwald | |
| 2007/0150029 A1* | 6/2007 | Bourget | A61N 1/37247 607/62 |
| 2008/0132801 A1 | 6/2008 | Logier | |
| 2008/0311406 A1 | 12/2008 | Bonnet et al. | |
| 2009/0292180 A1* | 11/2009 | Mirow | G06F 19/363 600/301 |
| 2010/0249556 A1 | 9/2010 | Sethi | |
| 2011/0066042 A1 | 3/2011 | Pandia et al. | |
| 2011/0112420 A1 | 5/2011 | Nagata | |
| 2012/0123232 A1* | 5/2012 | Najarian | A61B 5/0022 600/345 |
| 2013/0053722 A1* | 2/2013 | Carlson | A61B 5/7264 600/554 |
| 2014/0123912 A1 | 5/2014 | Menkes | |

OTHER PUBLICATIONS

"Heart rate variability: standards of measurement, physiological interpretation and clinical use" European Heart Journal vol. 17, pp. 354-381, 1996.

Schafer, Axel et al "How accurate is pulse rate variability as an estimate of heart rate variability?," International Journal of Cardiology, vol. 166, pp. 15-29, 2013.

Choi, Jongyoon et al "Development and Evaluation of an Ambulatory Stress Monitor Based on Wearable Sensors," IEEE Transactions on Information Technology in Biomedicine, vol. 16, No. 2, pp. 279-286, 2012.

Long, Xi et al "Single-Accelerometer-Based Daily Physical Activity Classification", 31st Annual International Conf. of The IEEE EMBS, 2009.

Logier, R. et al "PhysioDoloris: a monitoring device for Analgesia / Nociception balance evaluation using Heart Rate Variability analysis," in 2010 Annual International Conference of the IEEE Engineering in Medicine and Biology Society (EMBC), 2010, pp. 1194-1197.

Logier, R. et al "Pain / Analgesia evaluation using heart rate variability analysis," in 28th Annual International Conference of the IEEE Engineering in Medicine and Biology Society, 2006. EMBS '06, 2006, pp. 4303-4306.

Janda, M. et al "Design and implementation of a control system reflecting the level of analgesia during general anesthesia," Biomed Tech, 2013,vol. 58, No. 1, Abstract Only.

\* cited by examiner increasing pain

WEARABLE PAIN MONITOR USING ACCELEROMETRY

FIELD OF THE INVENTION

The present invention relates to a monitoring apparatus and a corresponding monitoring method for monitoring pain of a user.

BACKGROUND OF THE INVENTION

Pain is a feeling triggered in the nervous system that can range from mild, localized discomfort to agony. Pain has both physical and emotional components. Its physical part results from nerve stimulation. Pain may be contained to a discrete area, as in an injury, or it can be more diffuse, as in disorders like fibromyalgia. It is mediated by specific nerve fibers that carry the pain impulses to the brain where their conscious appreciation may be modified by many factors. Stress is the feeling of being under too much mental or emotional pressure. Common signs of stress include sleeping problems, sweating, loss of appetite and difficulty of concentrating. The identification of pain and stress periods may be helpful in diagnosing health issues. Pain in unconscious patients is different, since patient feedback cannot be retrieved.

According the definition by the International society for the study of pain the term "pain" may relate to "an unpleasant sensory and emotional experience associated with actual or potential tissue damage, or described in terms of such damage". According to the definition of The American Institute of stress the expression "stress" may describe a highly subjective phenomenon which can be thought of "the non-specific response of the body to any demand for change". "Discomfort" is also a subjective phenomenon and may relate "to the opposite of feeling comfortable".

Due to the very similar nature of the terms "pain", "discomfort" and "stress", the term "pain" as used in this document is for simplicity reasons used as a generic term which shall also encompass discomfort and stress.

Due to the subjective nature of feeling or experiencing pain, monitoring is usually based on self-reporting and observational/behavioral data. It is clear that such subjective measures are difficult to evaluate and to generalize. Accordingly, there are several efforts to measuring pain using physiological data which are related to the sympathetic/parasympathetic balance, and which are comparatively easy to collect and to quantify.

Physiological data indicative of pain may be obtained when a person/patient is subjected to pain. Accordingly, the effect of pain (including discomfort and/or stress) may cause the physiological parameters, such as blood pressure, pulse rate, respiration rate, respiration effort, or other parameters, alone or in combination, to change and often to increase. These changes of physiological parameters may be used as a basis for determining to which degree a patient/person experiences pain.

Pain monitoring and also stress monitoring may be performed by employing a visual analog scale that requires the patient to estimate the level of pain, discomfort and/or stress. The required attention of the patient towards feeling pain may bias this estimation, making the assessment unreliable. Reliability can be increased by unobtrusively measuring a parameter that reflects the level of pain, discomfort and/or stress and does not require the attention of the patient.

The quantification of pain and stress has been a clinical need for a long time. Different approaches have been used for this purpose including, for example, pulse transit time (PTT) which has been employed for measuring arousal and stress. Electrocardiogram (ECG) electrodes and photoplethysmography (PPG) have been used to estimate PTT from heart to hand. Increasing in PTT hereby indicates stress and pain. Alternative methods rely on a combination of PPG with galvanic skin response (GSR) for pain monitoring. Frequency features of heart rate variability obtained from ECG may be also employed. All these approaches are a function of sympathetic or parasympathetic activity.

US Publication No. 2011/0112420 A1 to Nagata (patented) discloses a device for objectively judging pain. The device comprises an electrocardiographic information acquiring unit which acquires a peak-relevant value such as the peak value of an R-wave for every cycle from an electrocardiogram. Pain is judged based on fluctuation related to the peak-relevant value and output.

WO 2007/052108 A2 discloses a method and system for monitoring vital signs for the prediction and treatment of physiological ailments. The system may detect changes in respiration rate, heart rate, and body motion indicating that a patient is suffering from pain. A motion sensor may be provided from which signals resulting from respiratory motion and heart beat may be derived.

US Publication No. 2014/0123912 A1 to Menkes (patented) discloses a system for monitoring vital signs of a pet animal. A suspicion of seizure may be determined based on sound, pulse, and respiration. Accelerometers may be used for measuring bioparameters of the pet animal including resting patterns, activity patterns, moving patterns, and position patterns.

Although the above mentioned approaches take use of vital signs, none of them are actually unobtrusive as they are all based on a use of current modalities which are usually derived from an ECG with a functional heart, i.e. a heart producing output upon contraction. For instance sticky ECG electrodes, a SpO2 sensor at the finger, and heavy blood pressure cuffs are used. Alternatively, GSR patches at the hand/wrist are employed. There is a need for an unobtrusive means of pain, stress and arousal monitoring which may have a wide range of applications, on post-operative recovery to chronic pain monitoring at home. Other problems of the known systems for measuring pain/stress reside in the usage of a large number of sensors which is burdensome to the patient, cumbersome as well as inconvenient during normal daily activity.

SUMMARY OF THE INVENTION

It is an object of the present invention to provide an unobtrusive device and method for monitoring pain of a user. Advantageously such an unobtrusive means of pain monitoring has a wide range of applications, before and during surgery and from post-operative recovery to chronic pain monitoring at home. Accordingly, operation of the device shall not demand particular skills to the user. Rather to the contrary, operation thereof needs to be self-explanatory. Another objective is the provision of an objective means of pain/stress scoring system which may be easily used by the patient and which does not require a high degree of attention. Still another objective resides in the provision of a device and method which may be easily used during normal daily activities. Still another objective is facilitating following up of pain development by a third person, such as a medical practitioner.

In a first aspect of the present invention a device for monitoring pain of a user is presented. The device comprises a receiving unit for receiving an accelerometer signal from an accelerometer sensor worn by the user, wherein the accelerometer signal comprises components of a pulse signal and components of a respiration signal. The device further comprises a processing unit which is configured to: derive the pulse signal and the respiration signal from the accelerometer signal; adapt the pulse signal based on the respiration signal in order to obtain a corrected pulse signal; and derive a pain descriptor based on the corrected pulse signal.

In another aspect of the present invention a method for monitoring pain of a user is presented. Said method comprises the following steps:

receiving an accelerometer signal from an accelerometer sensor worn by the user, wherein the accelerometer signal comprises components of a pulse signal and components of a respiration signal;

deriving the pulse signal and the respiration signal from the accelerometer signal; adapting the pulse signal based on the respiration signal in order to obtain a corrected pulse signal; and deriving a pain descriptor based on the corrected pulse signal.

In yet further aspects of the present invention, there is provided a computer program which comprises program code means for causing a computer to perform the steps of the method disclosed herein when said computer program is carried out on a computer.

Additionally a non-transitory computer-readable recording medium may be provided that stores therein a computer program product, which, when executed by a processor, causes the method disclosed herein to be performed.

Preferred embodiments of the invention are defined in the dependent claims. It shall be understood that the claimed method, computer program and recording medium have similar and/or identical preferred embodiments as the claimed device and as defined in the dependent claims.

The gist of the present invention is based on the finding that an accelerometer signal is sufficient for providing quantification of pain. It shall be noted again that the term "pain" as used in the appended claims also encompasses "discomfort" and "stress", as all of these effects cause a similar, measurable changes of physiological parameters, such as changes of the blood pressure, pulse rate, respiration rate, respiration effort, or other vital sign parameters, alone or in combination.

Accordingly, a simple device and method may be provided, wherein signals from a single accelerometer sensor are used. The accelerometer sensor is worn by the user which includes attaching the accelerometer sensor to the user's skin using a wearable device or implanting the accelerometer sensor in the user, such as below the user's skin. Preferably, the accelerometer is embedded in a wearable device such as a patch, a watch, glasses or an item of clothing.

The accelerometer signal comprises components of a pulse signal and components of a respiration signal. The pulse signal and respiration signal are extracted from the accelerometer signal, and the pulse signal is adapted based on the respiration signal in order to obtain a corrected pulse signal which has been found to represent a suitable descriptor not only for pain (including also discomfort and/or stress). A pain descriptor is derived based on the corrected pulse signal. Preferably, a stress descriptor and/or discomfort descriptor is also comprised in that the present method comprises the step of deriving one or more of a pain descriptor, discomfort descriptor and stress descriptor based on the corrected pulse signal. Likewise, the processing unit of the present device is adapted to derive one or more of a pain descriptor, discomfort descriptor and stress descriptor based on the corrected pulse signal.

In the context of the present invention pain is understood to encompass stress and discomfort. Accordingly, device and method may be directed to monitoring one or more of pain, discomfort and stress. In the line with this also the pain descriptor is regarded a measure comprising stress descriptor and discomfort descriptor.

"Deriving a pain descriptor based on the correct pulsed signal" as used herein includes either deriving the pain descriptor from the corrected pulse signal (i.e. from the corrected pulse signal alone), or deriving the pain descriptor from the corrected pulse signal and the respiration signal, in particular from the relationship between the corrected pulse signal and the respiration signal. Discomfort descriptor and/or stress descriptor may be assessed likewise, i.e. from the corrected pulse signal alone or from the corrected pulse signal and the respiration signal, in particular from the relationship between the corrected pulse signal and the respiration signal. Said relationship may be assessed, for example, by a correlation or a coherence of the two signals.

Alternatively, segments of the corrected pulse signal or the ratio of high-low frequency components of the corrected pulse signal may be employed for deriving a pain descriptor. Deriving the pain descriptor may encompass weighting of the respiration signal with respect to the pulse signal, or deriving a feature that incorporates the relationship between these two signals (via correlation, coherence or other methods). Alternatively or in addition, deriving the pain descriptor encompass regression analysis. Preferably, the pulse signal is the pulse rate signal. I will be understood that discomfort descriptor and/or stress descriptor may be derived likewise.

Heart rate variability is in part the result of respiration. During inspiration the thorax expands, creating a negative pressure, drawing blood into the thorax, creating a bigger cardiac pre-load, causing a shorter R-R' interval/time because the contraction takes place earlier in response to the increased preload. The respiratory variation can be extracted when it is a known variation, i.e. during ventilation. The present invention is based on the finding that addition of respiratory measurement based on an accelerometer signals may replace this.

Accordingly, the device and method make use of already existing wearable devices for measuring accelerometer signals rendering them suitable for use during normal daily activities of a patient in an unobtrusive manner.

A series of filters may be used to derive the (instantaneous) pulse signal and respiration signal from the accelerometer signal. Pulse signal and respiration signal may be transferred to the frequency domain (using for instance Fast Fourier Transforms), or time-frequency domain (using for example Windowed Fourier Transforms, Wigner-Ville or Wavelet Transforms). The effects of respiration may be filtered. One or more peaks may be detected within the accelerometer signal in order to derive the pulse signal and the respiration signal from the accelerometer signal.

A temporal approach may be also employed to track both pulse and a respiration signal over time. This could include, for example, a Kalman filter, or a Hidden Markov Model.

In case the pulse signal is derived and corrected, consecutive pulses may be used to derive the pulse variability. This strongly correlates to the heart rate variability, in particular when the subject is at rest. After filtering out the effects of respiration, pulse variability may be employed for the calculation of features that can best reveal the influence of pain, discomfort and stress. The effects of respiration may be removed or filtered out, for example, by using a Notch filter in the frequency domain around the human respiration frequency of approximately 0.2-0.4 Hz. This frequency can also be tracked in consecutive windows by using data modeling/tracking approaches like Kalman filtering to get an exact measurement and filter out erroneous data.

An optional step resides in deriving a pulse strength signal based on the corrected pulse signal as indicator of blood pressure and blood pressure change including a correction step due to increased or changed pulse rates. This measure may then be combined with the indicators measured from the pulse signal (either by weighting or by using a regression model). The combination of many parameters allows for less ambiguity to highlight pain/discomfort/stress periods.

Adapting a signal, such as pulse signal, based on another signal, such as the respiration signal, in order to obtain a corrected pulse signal has the meaning of employing any mathematical method or algorithm to the two signals, such as the pulse signal and the respiration signal, in order to obtain the corrected pulse signal. Suitable mathematical methods encompass subtraction, i.e. subtracting the respiration signal (or parts thereof), principal component analysis, or blind source separation from the pulse signal in order to obtain the corrected pulse signal. Such a corrected pulse signal may be essentially cleaned up, i.e. the components of the respiration signal are either completely or partially cancelled therefrom.

Deriving the pain descriptor, discomfort descriptor and/or stress descriptor may encompass weighting of the signals by giving either more weight or less weight to a particular signal. Alternatively or in addition, deriving the pain descriptor, discomfort descriptor and/or stress descriptor may encompass regression analysis.

A visual analog scale may be further used to assign values and/or symbols representing a degree of stress, discomfort and/or pain to the corrected pulse signal, segments thereof, or the ratio of high-low frequency components of the corrected pulse signal. The user/patient allocates his/her subjective impression of pain, discomfort and/or stress by entering a value from e.g. 0 to 10. For instance, 0 may correspond to a state without pain, discomfort and/or stress and 10 may correspond to a maximum of pain, discomfort and/or stress. The patient may use this visual analog scale and enter respective values in the device in case pain/discomfort/stress is/are experienced. In this way the device may be taught for a particular user and/or patient.

Alternatively, in an objective approach a pain descriptor, discomfort descriptor and/or stress descriptor may be already encompassed by the device or method based on medical information regarding to an average patient feeling or pain/discomfort/stress. Such information may further encompass age, medical history, and medication.

Still alternatively, both measures may be taken into account and the pain/discomfort/stress descriptor(s) may be derived from a subjective and objective approach and optionally weighting them.

According to a preferred embodiment of the present invention, the device further comprises the accelerometer sensor for measuring the pulse signal and the respiration signal. Preferably, a single accelerometer sensor is employed wherein the sensor is further adapted to provide a corresponding plurality of acceleration signals. Alternatively, two, three, four, five or more accelerometer sensors may be used, each of them adapted to provide a one or more acceleration signals. Measuring a plurality of acceleration directions is preferred since this offers the possibility to determine a precise acceleration signal. The acceleration sensor may, for example, comprise a multi-axial accelerometer which is adapted to generate a movement signal indicative of the acceleration along different spatial axis. The multi-accelerometer is preferably a tri-accelerometer adapted to generate a movement signal that comprises three accelerometer signals indicative of acceleration along three orthogonal spatial axes. For example, tri-accelerometers named Bosch BMA355, ST Microelectronics NIS3DSH, or ST Microelectronics LIS344ALH or Kionix KXM52 or LIS302SG can be used. However, also other kinds of multi-accelerometers can be used for generating accelerometer signal indicative of the acceleration along different spatial axis.

The number of accelerometer sensors is not particularly limited and may comprise for instance 2, 3, 4, 5, 6, 7, 8 different accelerometer sensors. Use of a single or low number of accelerometer sensors permits a rather simple device which is easy to use. Upon using several accelerometer sensors which are separated by a distance, i.e. some centimeters, such as 3, 4, 5, 6, 7, 8, or 10 centimeters, different signals for each of said accelerometer sensor is generated which can help filter out motion signals and get better pulse and respiration signals. Since blood pressure and blood pressure variations are also indicative of pain, it is further possible to derive pulse transit time measurements as BP surrogate by applications of several accelerometer sensors at different locations. The use of three accelerometer sensors, in particular two accelerometer sensors, is preferred due to the above mentioned reasons.

The one or more accelerometer sensors may be worn by a person, for instance on the sub-clavian chest area or on the abdomen below the diaphragm. In case several accelerometer sensors are used, they are space apart from each other at a distance. As already indicated above, the one or more accelerometer sensors may measure the pulse signal and the respiration signal. In addition, said one or more sensors may be used for measuring the activity level signal.

According to a further embodiment of the present invention the processing unit is further configured to transform the accelerometer signal to the frequency-domain or time-frequency-domain in order to derive the pulse signal and the respiration signal from the accelerometer signal. Transforming the accelerometer signal to the frequency domain may be performed, for example, by using Fast Fourier Transforms. Transferring to the time-frequency domain may be performed for example by using Windowed Fourier Transforms, Wigner-Ville or Wavelet Transforms. Effects of respiration may be filtered out. The effects of respiration may be filtered out, for example, by using a Notch filter in the frequency domain around the human respiration frequency of approximately 0.2-0.4 Hz. This frequency can also be tracked in consecutive windows by using data modeling/tracking approaches like Kalman filtering to get an exact measurement and filter out erroneous data. Accordingly, the step of filtering out a respiration signal or segments thereof may be encompassed.

Preferably a Fourier Transform that transforms a time series into a frequency spectrum is employed. Either, advantageously for low latency and a quick display, a temporal separation of wave form features, such as temporal peak-to-peak separation can be evaluated. Optionally, an average value of wave form features is displayed. Duration of averaging can be adapted based on a variation of the temporal separation of the wave form features.

According to another embodiment of the present invention, the processing unit is configured to detect one or more peaks within the accelerometer signal in order to derive the pulse signal and the respiration signal from the accelerometer signal. Peak detection may be performed by any suitable method and comprises for instance the use of conventional threshold and slope change detection algorithms and statistical methods for relative peak detection.

According to still another embodiment of the present invention the processing unit is configured to subtract the respiration signal from the pulse signal in order to obtain the corrected pulse signal. The respiration signal may be also weighted before subtracting from the pulse signal in order to obtain a corrected pulse signal still encompassing a part of the respiration signal.

According to an embodiment of the present invention the processing unit is further configured to determine pulse variability and/or a pulse strength based on the corrected pulse signal; and to derive the pain descriptor. Accordingly, the present device and system account for temporal changes of the pulse rate by determining pulse variability, i.e. the first deviation of the pulse rate (signal), and/or the amplitude of the pulse rate (signal) by determining pulse strength. Deriving one or more of the pain descriptor, discomfort descriptor and/or stress descriptor, such as the pain descriptor and/or the stress descriptor, may encompass weighting of the pulse variability and/or a pulse strength by giving either more weight or less weight. Alternatively or in addition, deriving the pain descriptor, discomfort descriptor and/or stress descriptor may encompass regression analysis. Pulse variability signal and/or activity level signal may be provided by an accelerometer sensor. In addition, the activity level signal may be provided by a GPS tracker which affords time resolved movement profiles of the user. Hence, the user's various activities may be better distinguished.

Analysis of movement patterns indicating pain and progression of pain levels may be also performed. This may be either accomplished through actigraphy, i.e. monitoring of rest/activity cycles, during activities of daily living or during standardized movement tests, such as post-surgical rehabilitation routines. Actigraphy may be accomplished by employing one or more actimetry sensors providing an actimetry signal. The present device and method may be further configured for receiving the actimetry signal(s) provided and adapting the pulse signal in addition to the respiration signal on the basis of the actimetry signal(s) in order to obtain a corrected pulse signal. The corrected pulse signal may be than used for deriving pain/discomfort/stress descriptors. The actigraphy information can also be used to identify activity context. Thus the pain/discomfort/stress descriptors can be analyzed in conjunction with the activity that is taking place. An example is: knowing a patient is getting out of bed after surgery, the pain descriptor can then be related to this exact activity that could be causing a stress on the wound.

Pulse strength may serve as indicator of blood pressure and blood pressure change including a correction step due to increased or changed pulse rates. The pulse strength may be therefore used for obtaining an improved pulse signal. The combination of many parameters in general allows for less ambiguity to highlight pain/discomfort/stress periods.

According to another embodiment of the present invention, a GPS tracking device for providing a tracking signal of the user may be provided, wherein the processing unit is further configured to: determine an activity level of the user based on the tracking signal and the accelerometer signal; and derive the pain descriptor additionally based on the activity level of the user. The GPS tracking device enables more accurate estimation of the activity being performed by the patient in case actigraphy information are used as well. This in turn improves the reliability of the device as the effect of context and activity on pain/discomfort/stress response is considered. GPS tracking devices are well known in the art. Actigraphy information may be either obtained by an actigraphy unit attached to the user. An actigraphy unit may comprise one or more actigraphy sensors adapted to monitor one or more of temperature, ambient light, sound level, tremor, and skin resistance. Alternatively, the one or more accelerometer sensors may be adapted to provide actigraphy information, such as information relating to the movement/activity of the user.

According to still another embodiment of the present invention, the processing unit is further configured to: determine a breathing rate and/or a breathing pattern based on the breathing depth; and derive the pain descriptor additionally based on the breathing rate and/or the breathing pattern. In the same manner also discomfort descriptor and/or stress descriptor may be derived. Breathing depth is related to the size of the negative pressure in the thorax. The measured breathing/respiration rate may be determined by taking into account, for instance, that shortness of breath is linked to sudden types of pain and pain severity. In addition, the breathing pattern on the patient may be analyzed, such as shallow breathing following a rib contusion or thoracic surgery. This further improves and enhances the reliability of pain detection. Breathing pattern and/or a breathing rate may be determined by using conventional sensors.

According to an embodiment of the present invention, a calibration unit may be comprised for calibrating the pain descriptor. Discomfort descriptor and/or stress descriptor may be calibrated likewise. Calibrating may be, for instance, accomplished by providing an input, wherein the user may enter the pain/discomfort/stress he/she experiences in particular situation. Such an input may be for example a number from 0 to 10 wherein 0 reflects that the user experiences no pain, whereas 10 indicate that the user experiences maximum pain. It will be appreciated that other scales with other gradation may be employed. The scale may be further provided with symbols for improved understanding of the underlying meaning. The user may, for instance, wear the device during normal activity and enter pain/discomfort/stress he/she experiences according to the current situation. Such pain/discomfort/stress causing situations may be also provoked. In this way, the user may enter for instance 5 for a medium severe pain/discomfort/stress and this value is then assigned to a pain/discomfort/stress descriptor value.

Particular pulse signals and respiration signals may by assigned to a particular event, i.e. a sensation of feeling a particular level of pain/discomfort/stress, stored and used as reference signals in case of a similar future event. The user may repeatedly teach the device in order to obtain more reliable results which may also consider the particular situation which may be reflected not only by instantaneous pulse signal and respiration signal but also the development of pulse signals and respiration signals over a period of time, such as 1 second to 1 hour, preferably, 1 minute to 30 minutes, or 10 to 20 minutes.

According to another embodiment of the present invention, an output unit may be comprised for displaying the pain descriptor. Discomfort descriptor and/or stress descriptor may be displayed likewise. Output of the pain descriptor, discomfort descriptor and/or stress descriptor may be performed by showing a number and/or a symbol. In addition, displaying may encompass providing an audible or tactile signal which provides the user to information about the pain/discomfort/stress descriptor experienced. The output unit may also provide the pain descriptor and/or stress descriptor to a medical practitioner. In addition or alternatively, the output unit may be adapted for providing an alarm signal to the user in case a pain, discomfort and/or stress descriptor reaches a critical level. Such a critical level may be defined by inputting for instance a threshold value for the pain, discomfort and/or stress descriptor.

In general, some parts of the device may be located remote from each other. For example, the optional output unit (and optionally the input unit) may be in form of an app for e.g. a mobile phone. An "app" is used herein as a piece of software which can run on the internet, a computer, a mobile phone or on other electronic devices. Alternatively, the sensor may be remote from the receiving unit and processing unit and optional output unit. In addition, there may be more than one output unit, such as two or three output units. This permits not only the user to prosecute changes of pain, discomfort and/or stress descriptors, but also allows e.g. a medical practitioner or care giver to follow up.

BRIEF DESCRIPTION OF THE DRAWINGS

These and other aspects of the invention will be apparent from and elucidated with reference to the embodiments described hereinafter. In the following drawings

DETAILED DESCRIPTION OF THE INVENTION

Figure 1:
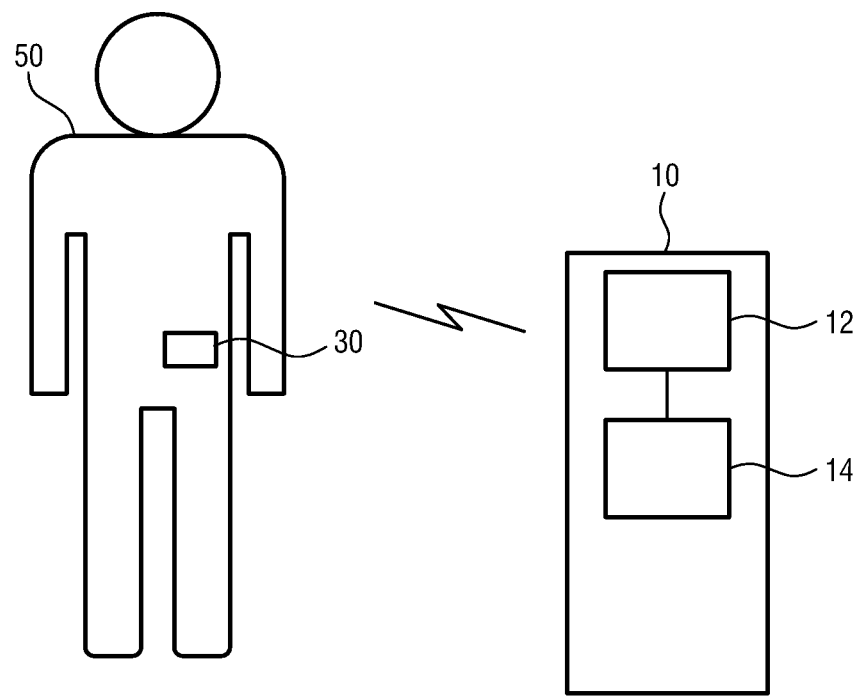
FIG. 1 shows a schematic drawing of a device of monitoring stress, discomfort and/or pain of a user.

FIG. 1 schematically shows a user/subject 50 wearing an accelerometer 30 connected to the abdominal area. It will be appreciated that the accelerometer 30 may be worn at other parts of the human body including, for example, the chest, such as the sub-clavian part of the chest. Alternatively, the accelerometer 30 may be also implanted below the skin at any of these locations. The user 50 may also wear one or more accelerometers 30. In addition, the user may wear other sensors than an accelerometer. The accelerometer sensor 30 preferably wirelessly transmits an accelerometer signal to a remote device 10 for monitoring stress, discomfort and/or pain of a user 50. It will be appreciated that the invention is not limited to wireless transmission of signals from the sensor 30 to the device 10, but also includes wired transmission. This may hold true for all or a part of the sensors employed herein. The device 10 may be also realized in the same housing together with the sensor 30 and does not need to be arranged remotely. The device 10 comprises a receiving unit 12 which receives the accelerometer signal from the accelerometer sensor 30. The accelerometer signal comprises components of a pulse signal, in particular components of pulse signal, and components of a respiration signal and is transferred to a processing unit 14 which derives the pulse signal and the respiration signal from the accelerometer signal; adapts the pulse signal based on the respiration signal in order to obtain a corrected pulse signal. A pain descriptor, discomfort and/or stress descriptor is derived based on the corrected pulse signal. Pain descriptor, discomfort and/or stress descriptor may be shown by an output unit.

Figure 2:
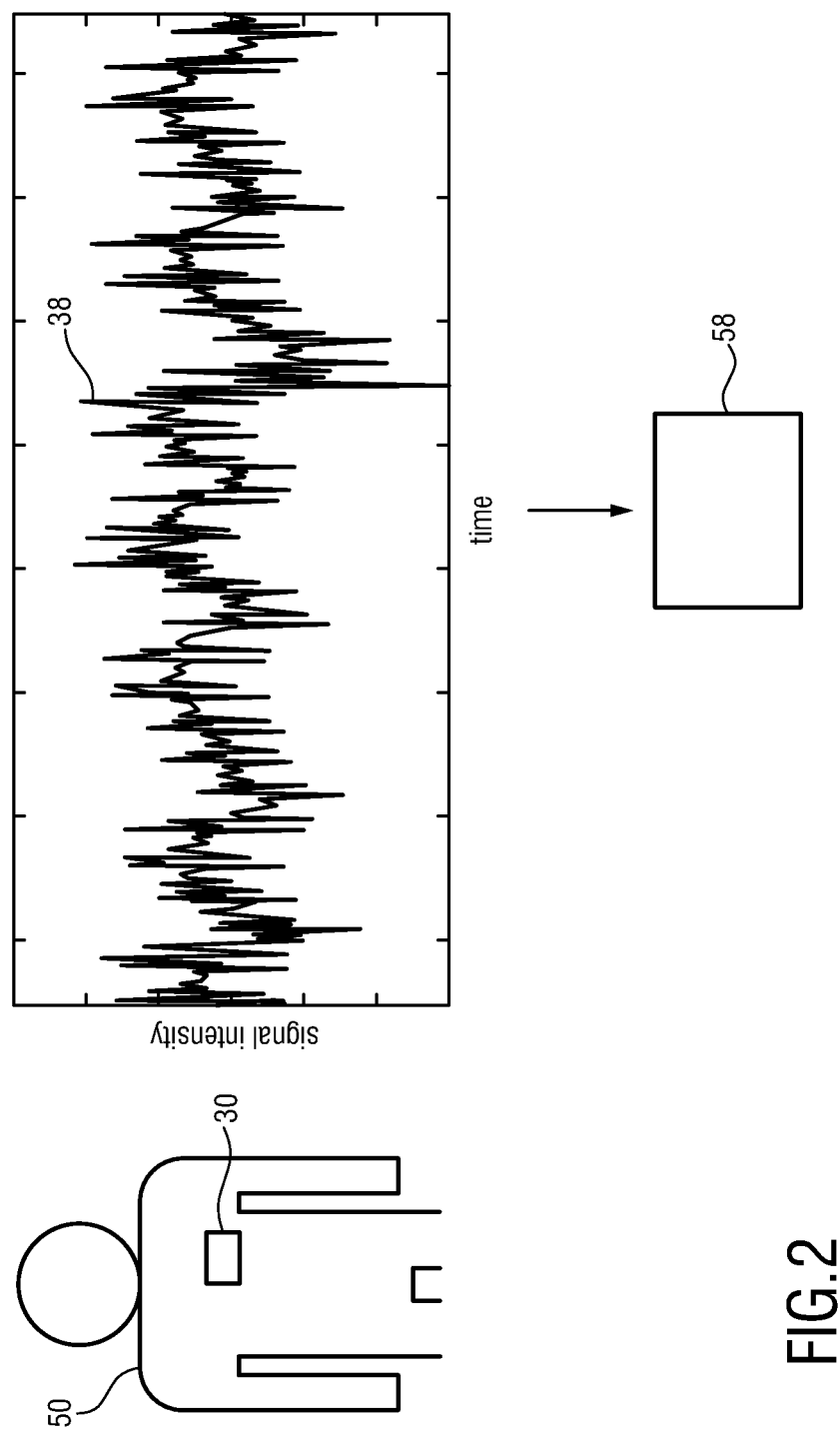
FIG. 2 schematically shows obtaining of a pulse signal and a respiration signal from a wearable accelerometer.

FIG. 2 schematically shows a subject 50 carrying a wearable accelerometer 30 on his/her chest. The accelerometer 30 measures and transmits a raw accelerometer signal 38 characterized by particular signal intensity over time. This accelerometer signal 38 is subjected to a filtering step for filtering out the pulse signal 20 and the respiration signal 22 which is indicated by box 58. A series of filters may be used for obtaining the instantaneous pulse signal and respiration signal. This may follow for instance the approach given in J. Muehlsteff et al., "Feasibility of Pulse Presence and Pulse Strength Assessment during Head-up Tilt Table Testing Using an Accelerometer located at the Carotid Artery" in Proceedings of EMBC 2014, 2014 for respiration extraction and instantaneous pulse rate and pulse variability.

Figure 3:
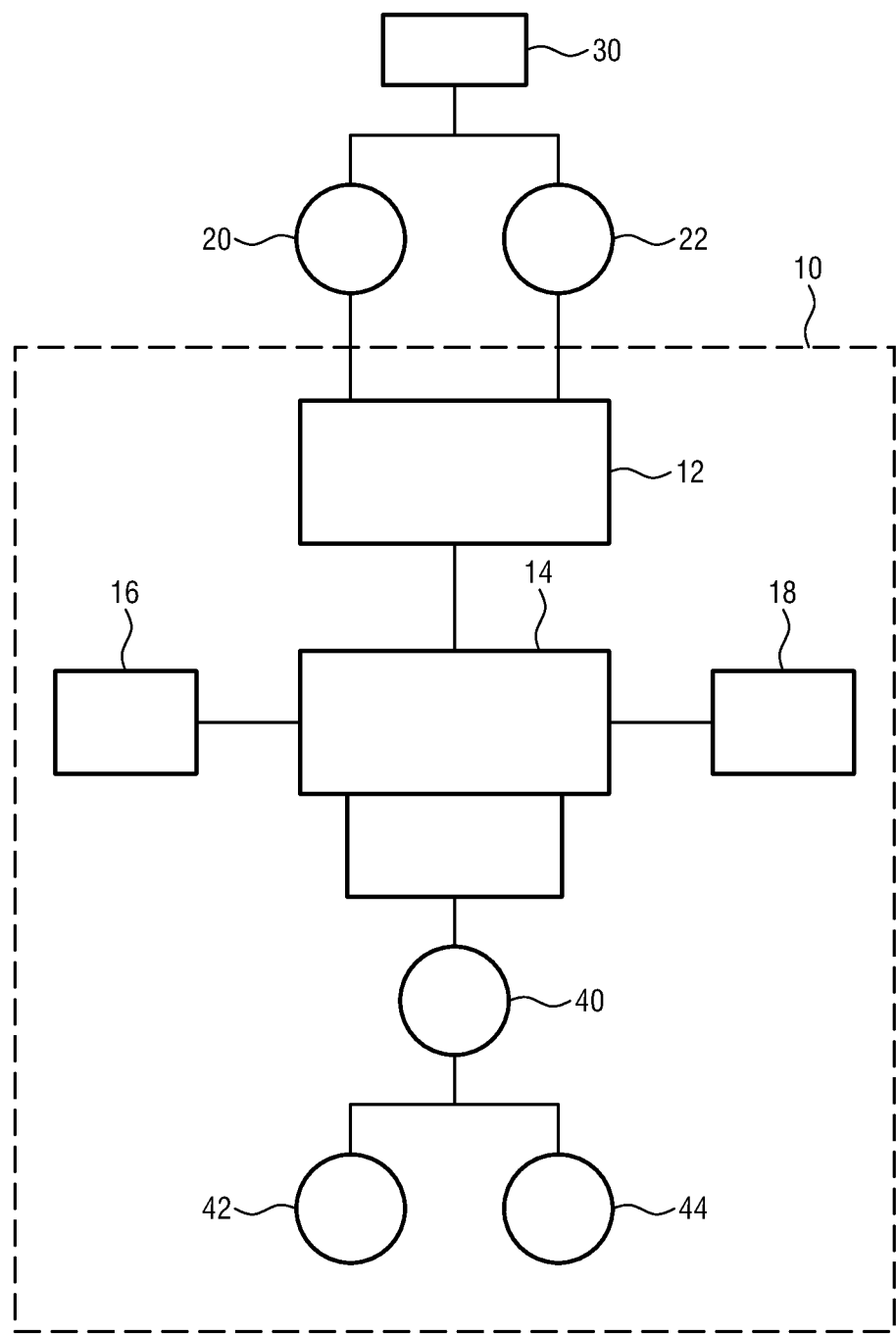
FIG. 3 schematically shows the main features of a device of monitoring stress, discomfort and/or pain of a user.

FIG. 3 schematically shows the main features of the device 10 of the present invention. One or more sensors, including the accelerometer sensor 30, provide the accelerometer signal 38 to the receiving unit 12 from which the processing unit 14 derives the pulse signal 20 and respiration signal 22. This may be performed by transferring the accelerometer signal 38 to the frequency domain or time-frequency domain and performing a frequency peak detection. The processing unit 14 further adapts the pulse signal 20 based on the respiration signal 22 for obtaining a corrected pulse signal 40. According to a preferred embodiment of the present invention, this is done by subtracting the respiration signal 22 from the pulse signal 20. A temporal approach may be alternatively employed for tracking both the pulse and the respiration signal over time. The effects of respiration are thus filtered out. However, the respiration signal 22 may also be used as a further refinement of the pain/discomfort/stress assessment.

Figure 5:
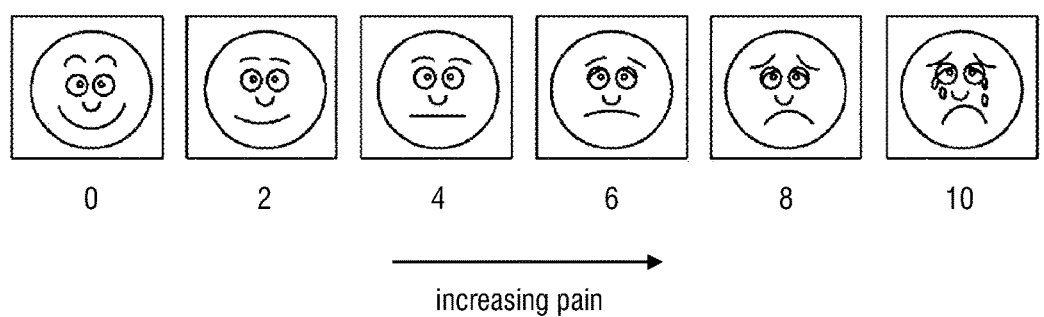
FIG. 5 shows a visual analog scale which may be used for assessing pain/discomfort/stress of a user.

The pulse signal 20, in particular a number of consecutive pulses, may be further used for deriving determining pulse variability, which is normally strongly correlated to heart rate variability. Processing unit 14 is configured to determine a pulse variability and the pulse strength based on the corrected pulse signal 20; and to derive the pain descriptor 42, discomfort descriptor 46 and/or stress descriptor 44 from the pulse variability and the pulse strength. Pulse variability is used, after filtering out the effects of respiration, for calculation of features which reveal the influence of pain, discomfort and stress. The effects of respiration are filtered out by using a notch filter in the frequency domain around the respiration frequency of approximately 0.2 Hz-0.4 Hz. The respiration signal can also be tracked in consecutive windows by using data modeling/tracking approaches, such as Kalman filtering, to get an exact measurement and filter out erroneous data. In the next step the corrected pulse signal 40 is assigned to particular values of for example a visual analog scale (FIG. 5). The same or a similar scale may be used for quantifying stress. The assigned pain descriptor 42, discomfort descriptor 46 and/or stress descriptor 44 derived form the corrected pulse signal 40 are shown to the user 50.

The device 10 may further comprise a calibration unit 16 for entering for instance values from a visual analog scale, and/or other medical information for teaching the device 10. The results, i.e. the pain, discomfort and/or stress descriptor 42, 44, 46, may be displayed via output unit 18, to indicate pain/discomfort/stress the user 50 experiences.

Figure 4:
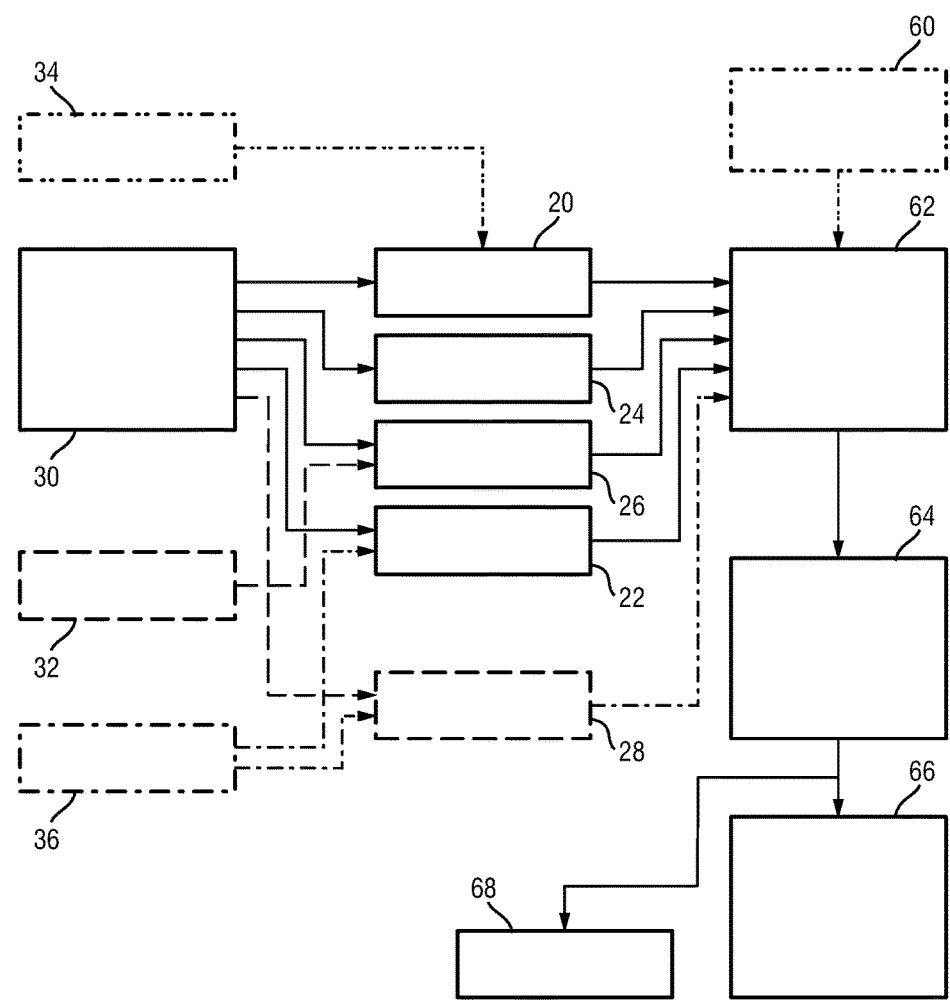
FIG. 4 shows a number of possible signals measured and further processing steps.

FIG. 4 schematically shows accelerometer sensor 30 providing pulse signal 20, pulse variability 24, activity level 26, and breathing rate or respiration signal 22. The device 10 may further comprise, in addition to the accelerometer sensor 30, a GPS tracking device 32, and optional means 34 for providing pulse signal 24 and/or means 36 for providing the breathing rate/respiration signal 22. Means 36 may be also used for providing breathing pattern 28. Means 34 and 36 may comprise well known sensors. Means 34 is for instance a photoplethysmographic sensor. Means 34, 36 and GPS tracking device 32 are used for improving accuracy of the corrected pulse signal 40. GPS tracking device 32 particularly assists in improving accuracy of activity level 26. Means 34 is used for improving accuracy of the respiration signal 22. In addition or alternatively, means 36 may be used for providing a breathing pattern 28 of user 50. Pulse signal 20, pulse variability signal 24, activity level signal 26, respiration signal 22, and breathing pattern 28 may subjected to a suitable transformation method for further processing. It may be furthermore assessed if the parameters 20, 22, 24, 26, 28 are in- or outside different pain/discomfort/stress severity level ranges (step 62). This may be further improved by the user by inputting for example data such as age, medical history, and medication (step 60) which data are used for defining the different pain/discomfort/stress severity level ranges in connection with the information given by the user 50 with respect to severity of particular pain/discomfort/stress experienced. The parameters are further rated and combined, via, for instance, regression to generate a pain score (step 64). The pain score may correspond to a particular value or symbol out of a pain score table (such as pain score table of FIG. 5 wherein to each of the symbols a particular degree, from 0 to 10, of severity of pain is assigned). The score or symbol is shown in step 66 either to a physician, caregiver, patient and/or family member and/or alternatively a respective pain warning and escalation alert (step 68) is given to the user in the need thereof. Discomfort and/or stress score may be generated, assessed and shown likewise as indicated above fro steps 64 to 68.

In conclusion, the device, and method presented herein reliably monitors not only pain but also stress and/or discomfort of a user. As an advantage, termination of the pulse signal and respiration signal involve a limited computational effect for low power consumption of the device. The use of a single accelerometer sensor may further contribute to low power consumption of the device.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or an does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A device for monitoring pain of a user, comprising:
    a receiving unit configured to receive an accelerometer signal from an accelerometer sensor configured to be worn in use by the user, wherein the accelerometer signal from the accelerometer sensor comprises components of a pulse signal and components of a respiration signal; and
    a processing unit which is configured to:
        derive the instantaneous pulse signal and the respiration signal from the accelerometer signal;
        adapt the pulse signal based on the respiration signal in order to obtain a corrected pulse signal; and
        derive a pain descriptor based on the corrected pulse signal.

2. The device according to claim 1, further comprising the accelerometer sensor for measuring the accelerometer signal.

3. The device according to claim 1, wherein the processing unit is further configured to transform the accelerometer signal to the frequency-domain or time-frequency-domain in order to derive the pulse signal and the respiration signal from the accelerometer signal.

4. The device according to claim 1, wherein the processing unit is configured to detect one or more peaks within the accelerometer signal in order to derive the pulse signal and the respiration signal from the accelerometer signal.

5. The device according to claim 4, wherein the processing unit is configured to subtract the respiration signal from the pulse signal in order to obtain the corrected pulse signal.

6. The device according to claim 5, wherein the processing unit is further configured to:
    determine a pulse variability and/or a pulse strength based on the corrected pulse signal; and
    derive the pain descriptor from the pulse variability and/or the pulse strength.

7. The device according to claim 6, further comprising a GPS tracking device for providing a tracking signal of the user, wherein the processing unit is further configured to:
    determine an activity level of the user based on the tracking signal and the accelerometer signal; and
    derive the pain descriptor additionally based on the activity level of the user.

8. The device according to claim 1, wherein the processing unit is further configured to:
    determine a breathing rate and/or a breathing pattern based on the respiration signal; and
    derive the pain descriptor additionally based on the breathing rate and/or the breathing pattern.

9. The device according to claim 8, further comprising a calibration unit for calibrating the pain descriptor.

10. The device according to claim 1, further comprising an output unit for displaying the pain descriptor.

11. A method for monitoring pain of a user, comprising:
    receiving an accelerometer signal from an accelerometer sensor configured to be worn by the user, wherein the accelerometer signal from the accelerometer sensor comprises components of a pulse signal and components of a respiration signal;
    deriving the instantaneous pulse signal and the respiration signal from the accelerometer signal;
    adapting the pulse signal based on the respiration signal in order to obtain a corrected pulse signal; and
    deriving a pain descriptor based on the corrected pulse signal.

12. The method according to claim 11, further comprising the step of transforming the accelerometer signal to the frequency-domain or time-frequency-domain in order to derive the pulse signal and the respiration signal from the accelerometer signal.

13. The method according to claim 11, further comprising the step of detecting one or more peaks within the accelerometer signal in order to derive the pulse signal and the respiration signal from the accelerometer signal.

14. The method according to claim 11, further comprising the step of subtracting the respiration signal from the pulse signal in order to obtain the corrected pulse signal.

15. A non-transitory computer program for causing a computer to carry out the steps of the method as claimed in claim 11, when said computer program is carried out on the computer.

* * * * *